(12) United States Patent
Tong et al.

(10) Patent No.: US 7,312,797 B2
(45) Date of Patent: Dec. 25, 2007

(54) REPRESENTING QUASI-HOMOGENOUS MATERIALS

(75) Inventors: Xin Tong, Beijing (CN); Jiaping Wang, Beijing (CN); Stephen S. Lin, Beijing (CN); Baining Guo, Beijing (CN); Heung-Yeung Shum, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 77 days.

(21) Appl. No.: 11/166,559

(22) Filed: Jun. 24, 2005

(65) Prior Publication Data
US 2006/0290719 A1 Dec. 28, 2006

(51) Int. Cl.
G06T 11/00 (2006.01)

(52) U.S. Cl. ...................................... 345/582

(58) Field of Classification Search .................. 345/582
See application file for complete search history.

(56) References Cited

OTHER PUBLICATIONS

Dana et al., "Reflectance and Texture of Real-World Surfaces", 1999, ACM, pp. 1-34.*

* cited by examiner

Primary Examiner—Almis R. Jankus
(74) Attorney, Agent, or Firm—Lee & Hayes, PLLC

(57) ABSTRACT

Representing quasi-homogenous materials is described. In one aspect, quasi-homogenous materials are modeled to generate a material model of a physical sample. The material model identifies how light is scattered by the quasi-homogenous materials. The material model, independent of an object model of the physical sample, provides information that is useful to texture surfaces of arbitrary types and sizes of mesh models (e.g., representing the physical sample or other objects) with the quasi-homogenous materials.

16 Claims, 7 Drawing Sheets

REPRESENTING QUASI-HOMOGENOUS MATERIALS

BACKGROUND

Many non-homogeneous translucent materials are composed of various substances evenly distributed throughout its volume. These quasi-homogeneous materials present a formidable challenge in realistic rendering because of their complex spatially variant sub-surface scattering properties. Furthermore, surface mesostructures typically complicate the appearance of quasi-homogeneous materials. Surface mesostructures not only produce surface reflections, but also affect how light enters and exits a material volume.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In view of the above, representing quasi-homogenous materials is described. In one aspect, quasi-homogenous materials are modeled to generate a material model of a physical sample. The material model identifies how light is scattered by the quasi-homogenous materials. The material model, independent of an object model of the physical sample, provides information that is useful to texture surfaces of arbitrary types and sizes of mesh models (e.g., representing the physical sample or other objects) with the quasi-homogenous materials.

BRIEF DESCRIPTION OF THE DRAWINGS

In the Figures, the left-most digit of a component reference number identifies the particular Figure in which the component first appears.

DETAILED DESCRIPTION

Overview

Figure 1:
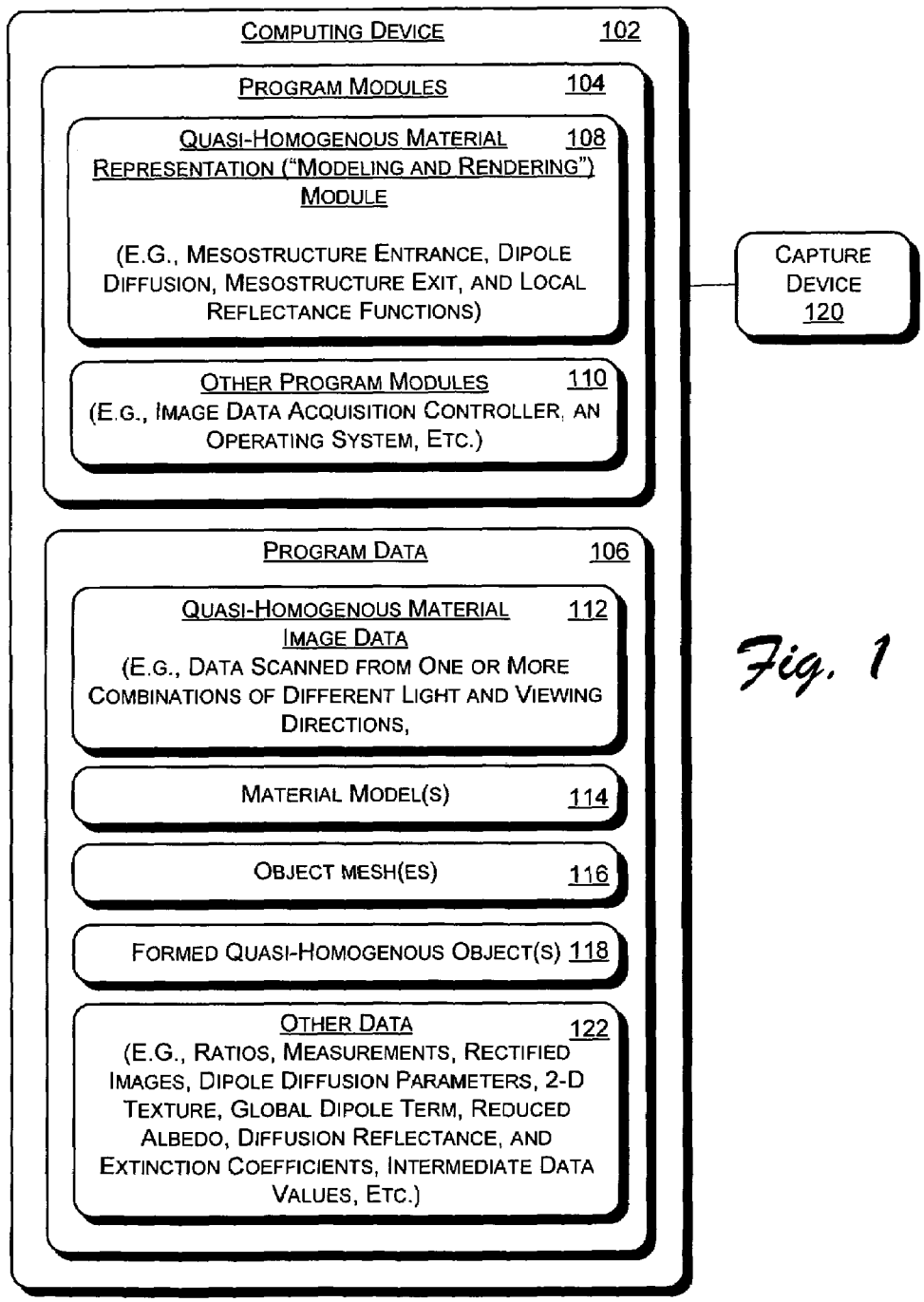
FIG. 1 shows an exemplary system for representing (e.g., modeling and rendering) quasi-homogenous materials.

Representing quasi-homogenous materials provides for modeling and rendering quasi-homogeneous materials based on a material representation which is acquired from physical samples. This material representation is applied to geometric models of any arbitrary shape. The resulting objects are efficiently rendered without expensive sub-surface light transport simulation. To emphasize its broad applicability to arbitrary geometric models, this representation is referred to as a material model to distinguish it from object models, which are typically used in image-based modeling and rendering of real-world objects. A material model describes how light is scattered by the material, while an object model captures the actual appearance of a specific physical object. Unlike a material model, an object model measured from a given translucent object cannot be applied to objects of other shapes, because the appearance of each surface point is not a local quantity but the result of light propagation within the whole object.

The material model utilized to represent quasi-homogenous materials is used to effectively analyze sub-surface scattering characteristics of quasi-homogeneous materials at two different scales. At a local level, the heterogeneity of a volume leads to non-homogeneous sub-surface scattering. At a larger scale, because of the even distribution of materials within a quasi-homogeneous volume, small neighborhoods centered at different points in the volume have a statistically similar material composition and distribution. For global sub-surface scattering at this larger scale, photon propagation is similar to that in a homogeneous material composed of particles whose scattering properties approximate the overall scattering of these volume neighborhoods.

Based on this observation of local heterogeneity and global homogeneity, the material representation includes four components: a homogeneous sub-surface scattering component for global light transport, a local reflectance function, a mesostructure entrance function, and a mesostructure exiting function. The last three components account for local scattering effects that include inhomogeneous local sub-surface scattering, surface reflections from mesostructure, and locally inhomogeneous mesostructure effects on light entering and exiting the material. In this implantation, the four components of this material model are acquired by capturing both laser stripe and halogen lamp images of a physical sample under multiple illumination and viewing directions, and then breaking down these images into appropriate components.

These and other aspects of representing quasi-homogenous materials are now described in greater-detail below with respect to FIGS. 1 through 7.

An Exemplary System

Although not required, representing quasi-homogenous materials is described in the general context of computer-program instructions being executed by a computing device such as a personal computer. Program modules generally include routines, programs, objects, components, data structures, etc., that perform particular tasks or implement particular abstract data types. While the systems and methods are described in the foregoing context, acts and operations described hereinafter may also be implemented in hardware.

FIG. 1 shows an exemplary system 100 for representing quasi-homogenous materials. In this implementation, system 100 includes a general purpose computing device 102. Computing device 102 represents any type of computing device such as a personal computer, a laptop, a server, handheld or mobile computing device (e.g., a cellular phone, personal digital assistant), and/or so on.

Computing device 102 includes program modules 104 and program data 106. Program modules 104 include, for example, quasi-homogenous material representation module 108 (hereinafter often referred to as "modeling and rendering module 108"), and other program modules 110 such as a quasi-homogenous image data acquisition controller in one implementation, an operating system, etc.

Modeling and rendering module 108 generates or receives quasi-homogenous material image data 112 ("image data 112") to create a material model 114 representing quasi-homogenous materials that comprise an object (a physical sample). Image data 112 is acquired by physical sampling of the object. Such physical sampling of the object to acquire image data 112 is described in greater detail below in the section titled "Exemplary Measurement System". Modeling and rendering module 108 applies the material model 114, under configurable lighting conditions, to one or more object meshes 116 of arbitrary size and shape to render one or quasi-homogenous objects 118. Accordingly, a quasi-homogenous object 118 is an object with texture of the quasi-homogenous materials that are represented by the material model 114, rendered onto the objects' surface.

Exemplary Quasi-Homogenous Material Representation

Before describing how an object is physically sampled to generate image data 112, this section describes modeling and rendering module's 108 exemplary representation of quasi-homogenous materials. Modeling and rendering module 108 utilizes the bidirectional scattering-surface reflectance-distribution function (BSSRDF) to provide a general model for light scattering from surfaces. The representation for quasi-homogeneous materials is based upon this function. More particularly, modeling and rendering module 108 computes outgoing radiance $L(\chi_o,\omega_o)$ at a surface point $\chi_o$ in direction $\omega_o$ by integrating the contribution of incoming radiance $L(\chi_i,\omega_i)$ for all incident directions $\omega_i$ over the surface A as follows:

$$L(\chi_o,\omega_o) = \int_A \int_\Omega S(\chi_i,\omega_i;\chi_o,\omega_o) L(\chi_i,\omega_i) d\omega_i d\chi_i.$$

Here, $d\chi_i = (n \cdot \omega_i) dA(\chi_i)$, where $(n \cdot \omega_i)$ is the cosine factor and $dA(\chi_i)$ is a differential area at $\chi_i$. The integral is separated into local and global contributions as follows:

$$L(\chi_o,\omega_o) = \int_{A_o} \int_\Omega S(\chi_i,\omega_i;\chi_o,\omega_o) L(\chi_i,\omega_i) d\omega_i d\chi_i + \int_{B_o} \int_\Omega S(\chi_i,\omega_i;\chi_o,\omega_o) L(\chi_i,\omega_i) d\omega_i d\chi_i,$$

wherein the local contribution is integrated over a small disk $A_o$ of radius $r_s$ around $\chi_o$ and the global contribution is aggregated from the rest of the surface $B_o = A - A_o$.

Figure 2:
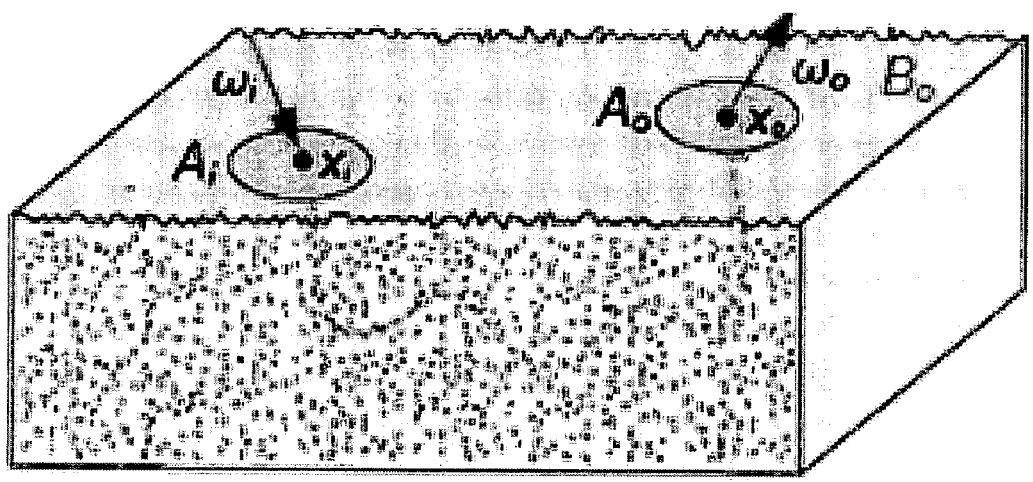
FIG. 2 illustrates light scattering geometry for quasi-homogenous materials.

FIG. 2 illustrates light scattering geometry for quasi-homogenous materials.

Since incident radiance $L(\chi_i,\omega_i)$ may be regarded as locally uniform over $A_o$, the local contribution $L_l(\chi_o,\omega_o)$ can be written as follows:

$$L_l(x_o,\omega_o) = \int_{A_o} \int_\Omega S(x_i,\omega_i,x_o,\omega_o) L(x_i,\omega_i) d\omega_i dx_i$$

$$\approx \int_\Omega R(x_o,\omega_i,\omega_o) L(x_i,\omega_i) d\omega_i$$

wherein $$R(x_o,\omega_i,\omega_o) = \int_{A_o} S(x_i,\omega_i,\omega_o) dx_i$$

is the local reflectance function. For illumination to be locally uniform, the distance of illuminants from the measured object is larger than the radius of a local heterogeneous area. (In another implementation, illumination is not locally uniform, and this non-uniformity is addressed by pre-filtering irradiance on the surface, or measuring point response functions within local areas).

For the global contribution $$L_g(\chi_o,\omega_o) = \int_{B_o} \int_\Omega S(\chi_i,\omega_i;\chi_o,\omega_o) L(\chi_i,\chi_i) d\omega_i d\chi_i, \quad (1)$$

the incoming radiance $L(\chi_i,\omega_i)$ undergoes significant scattering. Modeling and rendering module 108 approximates its impact at $\chi_o$ by an averaging effect as follows:

$$\int_{B_o} \int_\Omega \frac{1}{\pi r_s^2} \left[ \int_{A_i} S(x_i+r_i,\omega_i,x_o,r_o) dr_i \right] L(x_i,\omega_i) d\omega_i dx_i$$

where $A_i$ is a disk of radius $r_s$ around $\chi_i$ and $L(\chi_i,\omega_i)$ is locally uniform over $A_i$.

Further averaging over $A_o$ is performed to obtain the following:

$$\int_{B_o} \int_\Omega \frac{1}{\pi^2 r_s^4} \left[ \int_{A_i} \int_{A_o} S(x_i+r_i,\omega_i,x_o+r_o,\omega_o) dr_i dr_o \right] L(x_i,\omega_i) d\omega_i dx_i.$$

Notice that $$\int_{A_i} \int_{A_o} S(\chi_i+r_i,\omega_i;\chi_o+r_o,\omega_o) dr_i dr_o L(\chi_i,\omega_i)$$

is the radiance contribution from area $A_i$ to area $A_o$. Since a quasi-homogeneous material is homogeneous at a large scale and is optically thick, modeling and rendering module 108 applies the dipole diffusion approximation to this area-to-area contribution:

$$\int_{A_i} \int_{A_o} S(\chi_i+r_i,\omega_i;\chi_o+r_o,\omega_o) dr_i dr_o L(\chi_i,\omega_i)$$

$$\approx \pi^2 r_s^4 F_o(A_o,\omega_o) R_d(\chi_i,\chi_o) L(\chi_i,\omega_i) f(\omega_i)$$

where $R_d(\chi_i,\chi_o)$ is the diffuse reflectance given by the dipole approximation, $F_o(A_o,\omega_o)$ is the average outgoing Fresnel term over $A_o$ in direction $\omega_o$, and $f(\omega_i)$ is the mesostructure entrance function of the material, which essentially represents an average product of the incoming Fresnel term and cosine foreshortening factor over the surface area. The mesostructure entrance function is expressed independently of location since its average effect within a local region $A_i$ is taken to be uniform over the material surface.

Based on the above analysis for a local region $A_o$, it can be seen that $L_g(\chi_o,\omega_o)$ is proportional to the following dipole diffusion term:

$$L_g(\chi_o,\omega_o) \alpha \int_{B_o} \int_\Omega R_d(\chi_i,\chi_o) L(\chi_i,\omega_i) f(\omega_i) d\omega_i d\chi_i.$$

Such a dipole diffusion term is represented by component of FIG. 1.

The above relation can be rewritten as follows:

$$L_g(\chi_o,\omega_o) = \int_{B_o} \int_\Omega f_v(\chi_o,\omega_o) R_d(\chi_i,\omega_i) f(\omega_i) d\omega_i d\chi_i \quad (2)$$

by introducing a mesostructure exiting function $f_v(\chi_o,\omega_o)$ to modulate the average diffuse contribution of the dipole diffusion term according to the view-dependent effects at $\chi_o$, the local variation within $A_o$, and the outgoing Fresnel factor at $\chi_o$. From Eq. (1) and Eq. (2), the mesostructure exiting function is expressed as follows:

$$f_v(x_o, \omega_o) = \frac{\int_{B_o}\int_\Omega S(x_i, \omega_i, x_o, \omega_o)L(x_i, \omega_i)d\omega_i dx_i}{\int_{B_o}\int_\Omega R_d(x_i, x_o)L(x_i, \omega_i)f(\omega_i)d\omega_i dx_i}. \quad (3)$$

In summary, the outgoing radiance from a quasi-homogeneous material is formulated as follows:

$$L(\chi_o,\omega_o) = \int_\Omega R(\chi_o,\omega_i,\omega_o)L(\chi_i,\omega_i)\,(d\omega_i$$

$$+ \int_{B_o}\int_\Omega f_v(\chi_o,\omega_o)R_d(\chi_i,\chi_o)L(\chi_i,\omega_i)f(\omega_i)d\omega_i d\chi_i. \quad (4)$$

Based on this equation, modeling and rendering module 108 implements a material model 114 to represent quasi-homogeneous materials that includes four components: the local reflectance function $R(\chi_o,\omega_i,\omega_o)$, the mesostructure exiting function $f_v(\chi_o,\omega_o)$, the mesostructure entrance function $f(\omega_i)$, and the global dipole term $R_d(\chi_i,\chi_o)$. As described immediately below, all of these components are measured from real materials.

An Exemplary Measurement System

In measuring a material model, a laser beam could be used to illuminate a material sample, but its highly concentrated illumination results in large intensity differences between specular radiance and global scattering radiance. An extensive dynamic range presents an impediment to accurate radiance measurement. To diminish this problem, system 100 separately captures global and local scattering exhibited by quasi-homogenous materials using different types of lighting. Since global scattering does not contain specular reflections and exhibits an exponential falloff with increasing scattering distance, system 100 employs a laser to heighten its visibility. Specifically, system 100 utilizes a laser stripe instead of a laser beam to significantly accelerate the capture of image data 112, and substantially reduce the amount of image data 112. Although a laser stripe does not illuminate a local circular area as shown for $A_j$ in FIG. 2, a laser stripe can nevertheless be used for global scattering measurements. In acquiring local scattering, this exemplary implementation of system 100 utilizes a BTF measurement approach with lamps instead of lasers. This is because lamps provide uniform illumination with a relatively narrow dynamic range, and thereby reduces obscuration of texture details by specular reflections.

Image capture device 120 of FIG. 1 captures image data by physically sampling an object. In this implementation, computing device 102 is coupled to image capture device 120 to control image data capture operations of the image capture device 120. Such control is provided, in this implementation for example, by an image data acquisition controller portion of "other program modules" 110. In another implementation, computing device 102 is not coupled to image capture device 120. In this alternate implementation, image capture device 120 includes a separate controller to control capture of image data 112. In this alternate implementation, image data 112 is provided to computing device using any arbitrary method of data transfer.

Figure 3:
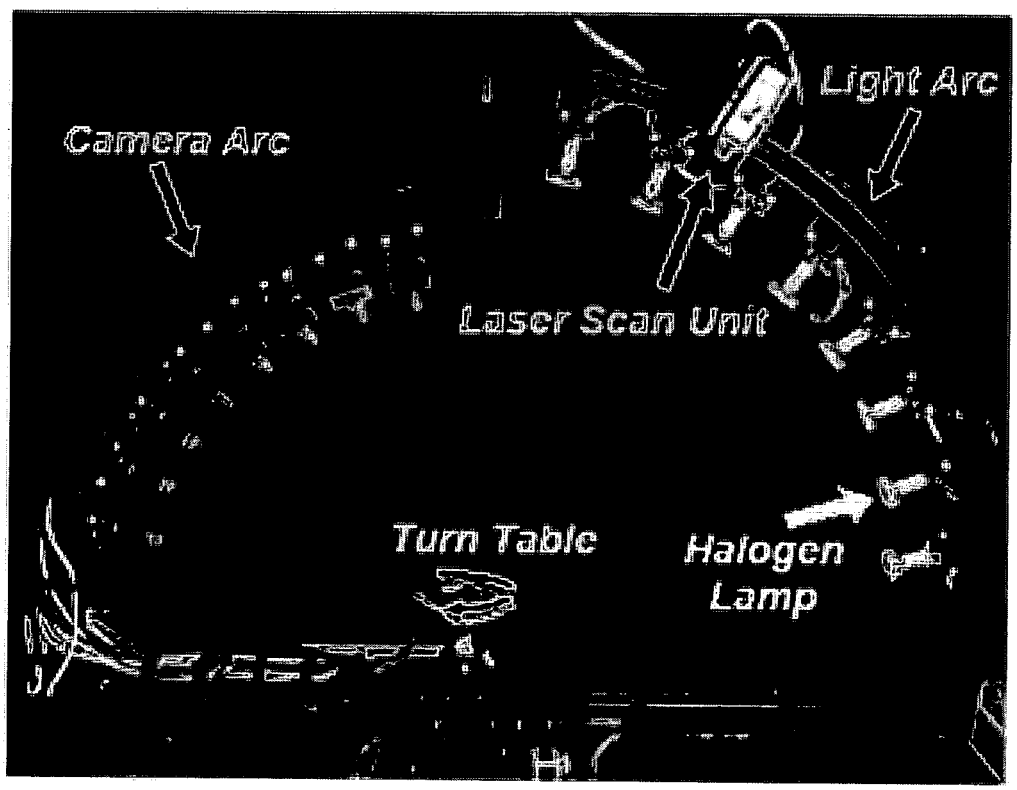
FIG. 3 shows an exemplary implementation of a capture device for imaging an object comprised of quasi-homogenous materials.

FIG. 3 shows an exemplary implementation of capture device 120 for imaging an object comprised of quasi-homogenous materials. In this exemplary implementation, capture device 120 includes a turntable, an imaging array, a lighting array and a laser scan unit, each of which are controlled by computing device 102. In this exemplary implementation, the cameras, lights, and laser unit are mounted on two concentric arcs centered around the turntable, which can be rotated by a stepping motor. On the flat surface of the turntable is placed the material sample (object) to be measured.

In this implementation, the cameras (i.e., imaging array) includes, for example, eight DragonFly™ cameras evenly mounted on a stationary arc. The bottom camera, as well as the bottom lamp, are not used in the capture process. This is because, in this exemplary implementation, the top surface of a thick sample is occluded from the bottom camera and the bottom lamp. In this implementation, each camera acquires 24-bit images (respective portions of image data 112), although other image depths can be used. A 24-bit image has a resolution of 1024×768. In this implementation, images are acquired at 3.75 Hz using different shutter speeds and the maximum aperture setting to create high dynamic range (HDR) images.

The lighting array (light arc) is mounted on the right arc of the capture device 120. In this exemplary implementation, the lighting array includes eight halogen lamps. This provides nearly directional light for samples on the turntable. In this implementation, the light arc is driven by another stepping motor that rotates it around the turntable center.

In this implementation, the laser scan unit of image capture device 120 includes one of three interchangeable 10 mw lasers (e.g., red: 650 nm, green: 532 nm, blue: 473 nm) with a line lens attached to produce a laser stripe. In this implementation, only one laser at a time can be attached to the laser control unit, so image measurement is iterated three times for the red, green, and blue lasers. In another implementation, all three lasers are attached to the laser control unit, so image measurement is iterated a single time for the red, green, and blue lasers. The laser scan unit can be manually fixed at any position on the light arc, and a controller adjusts the orientation of the laser to sweep a stripe over the surface of the sample.

For geometric calibration, the origin of the coordinate system utilized by system 100 is set at the center of the turntable, with the XY plane aligned with the flat surface. Before capture, the position of the light sources are calibrated (e.g., manually calibrated). For example, the intrinsic and extrinsic parameters of the cameras are calibrated. For photometric calibration, the response curves of the cameras are determined. Then for relative color calibration of the cameras, a standard color pattern is placed onto the turntable. Images are captured from each camera with light from a given lamp. To calibrate lamp illumination colors, an image is conversely captured from a given camera for a lamp.

To calibrate the laser stripes, the angle between the laser plane is calculated; defined as the plane containing the laser stripe and laser emission point, and the XY plane. To this end, a laser stripe is projected onto two planes of different heights. The offset of the laser stripe in the two planes from two recorded laser scan images is calculated. From this offset, the angle between the laser plane and the XY plane is derived. In this implementation and since the distance of the laser emitter from the turntable is much larger than the material sample diameter, all the laser planes in one scan are considered as being parallel.

Exemplary Material Model Acquisition

System 100 measures a material sample to generate image data 112. The material sample is measured using the laser stripe and lamp illumination in the process outlined in Table 1. It is assumed that the material sample is optically thick enough so that a negligible amount of light exits the bottom of the sample. In this implementation, any such transmitted light is absorbed (and ignored) with a black cloth set beneath the sample. In a different implementation, transmitted light that exits the bottom of a physical sample (e.g., the light absorbed by the black cloth) is accounted for in the generated material model 114.

TABLE 1

EXEMPLARY CAPTURE DEVICE IMAGE ACQUISITION

First Pass:

For all laser colors
        For all laser positions on arc
            For all light arc rotations
                Project a lasers strip on sample (object)
                For each laser scan position
                      Capture images from all cameras Second Pass:

For all laser colors
        For all turntable positions
            Project the lasers strip vertically on sample
            For each laser scan position
                Capture images from all cameras Third Pass:

For all light arc rotations
        For all lamps on the arc
            For all turntable rotations
                Capture images from all cameras From the acquired data set (a respective portion of image data 112), modeling and rendering module 108 separates appearance components that correspond to the elements of material model 114. The separation operations are performed to enable inverse rendering of dipole diffusion parameters and measurement of the texture functions. In the laser stripe images, global sub-surface scattering is clearly revealed, but its appearance is influenced by mesostructure entrance and exiting functions. To decouple these reflectance components, modeling and rendering module 108 takes advantage of their distinct directional dependencies: the mesostructure entrance function depending on light direction, the mesostructure exiting function on view direction, and dipole diffusion being directionally independent. Modeling and rendering module 108 subtracts the global components from the halogen lamp images, leaving the local reflectance function, which consists of local non-homogeneous sub-surface scattering and mesostructure surface reflections.

In the image capture procedure of Table 1, all laser images are rectified onto the reference plane of the material model 114, which is defined above the top surface of the sampled object. The top surface of the sampled object is considered to be globally flat, but may contain local mesostructures. In the rectification process, modeling and rendering module 108 identifies pixels on the laser stripe according to a prescribed intensity threshold, and to these pixels, module 108 fits a line. In this implementation, HDR images are not used in the rectification process. The obtained set of rectified images I(p,v,l) record for incoming flux from laser stripe l the measured radiance in direction v from 3D location p(x,y) on the reference plane, where p lies within a user-specified distance interval from l such that radiance from p results from global scattering and has an intensity that is sufficiently above the camera noise level. For purposes of exemplary illustration, such rectified images are shown as a respective portion of "other data" 122.

In this implementation, the measured material sample is considered to be optically thick, such that a negligible amount of light passes through the bottom surface. Only a central portion of the sample is measured to avoid edge effects such as light leakage through the sides.

An Exemplary Mesostructure Entrance Function

In the first step of the measurement process, image capture device 120 scans the sampled object with laser stripes emitted from different light directions. To this end, the laser is mounted at several positions along the light arc. For each position, the light arc is rotated to sampled angles to capture laser scan images at sampled viewing directions.

For a laser stripe projected from the vertical direction, the corresponding mesostructure entrance function value is set to equal one. From other incident light directions, modeling and rendering module 108 computes the mesostructure entrance function in relation to the vertical direction as follows:

$$f(\omega_i) = \sum_v \sum_p \sum_{l \in \omega_i} I(p, v, l) \Big/ \sum_v \sum_p \sum_{l \in \omega_0} I(p, v, l),$$

where the numerator aggregates images with laser lines from direction $\omega_i$, and the denominator sums images with laser lines from the vertical direction $\omega_0$. Although images from a single view are sufficient to solve for this function, modeling and rendering module 108 utilizes utilize several sparse viewing samples for greater robustness. In this implementation, 4×4 viewing samples are utilized.

Exemplary Dipole Diffusion Parameters

Referring to Table 1, and as shown in section titled "Second Pass", capture device 120 captures laser scan images from different viewing directions and under vertically projected illumination. This generates image data 112 utilized by modeling and rendering module 108 to compute the dipole diffusion parameters. For purposes of exemplary illustration, the dipole diffusion parameters are shown as a respective portion of "other data" 122. After the turntable is rotated to a desired sampling position, the light arc is rotated accordingly so that the sample is always scanned along the same direction. Capture device 120 utilizes all cameras to simultaneously-capture the appearance of the sample.

In this implementation, to fit the global dipole model to a particular data set, modeling and rendering module 108 utilizes an approximation to set the refraction index to 1.3 in dipole fitting. In other implementations, different approximations are utilized to set the refraction index to different value(s) as a function of the quasi-homogenous materials being sampled. In view of this approximation, modeling and rendering module 108 determines the global dipole term from two scattering properties: the reduced albedo $\alpha'$ and reduced extinction coefficient $\sigma'_t$. For purposes of exemplary illustration, these two scattering properties are shown as respective portions of "other data" 122. Directly fitting these two parameters to measured data is ill-conditioned. Instead, modeling and rendering module 108 first measures the total diffuse reflectance R of the material sample and derives the reduced albedo $\alpha'$. Then the reduced extinction coefficient $\sigma'_t$ is fit to the captured images.

In this implementation, the total diffuse reflectance is the ratio between the outgoing flux of the sample surface and incoming flux of a vertical laser stripe, expressed for stripe l from direction $\omega_0$ as follows:

$$\sum_p \sum_v I(p, v, l) = R \frac{k_1}{k_0} \phi - 0.03 \text{ in}$$

where $k_1$ is the laser stripe length on the sample, $\phi$ is the laser flux measured from a reference surface of known reflectance with laser stripe length $k_0$. It is assumed that the intensity of the laser stripe is constant along the line. The effect of the mesostructure exiting function is effectively removed by summing corresponding image pixels from the different viewpoints. For a more robust estimate, capture device 120 captures multiple laser stripe projections at different positions and then averages the resulting diffuse reflectance values. With the total diffuse reflectance, modeling and rendering module 108 solves for the reduced albedo $\alpha'$ of the material.

With the derived reduced albedo $\alpha'$, modeling and rendering module 108 solves for the material's reduced extinction coefficient $\sigma'_t$ by fitting the dipole model to the measured data. In fitting the dipole model, the same image set is summed over the viewing directions to eliminate mesostructure exiting function effects from the measured data:

$$I(p, l) = \sum_v I(p, v, l) = \sum_{p' \in l} R_d(p, p') \frac{\phi}{k_0}. \quad (5)$$

Additionally, modeling and rendering module 108 integrates the outgoing radiance of all points $p_d$ that are a distance d from the laser line to obtain the function as follows:

$$I(d) = \sum_{p_d} \sum_{p' \in l} R_d(p_d, p') \frac{\phi}{k_0}. \quad (6)$$

In this implementation, and since the double summation in Eq. (6) has no closed-form solution, modeling and rendering module 108 creates a virtual version of the laser stripe with the same incoming flux $$\frac{k_1 \phi}{k_0}$$

and render $I_D(d)$ from it using Eq. (6) and $\sigma'_t$ values sampled from 0.0 to 10.0, which covers most of the materials of interest. In another implementation, $\sigma'_t$ is sampled from different ranges. In this implementation, modeling and rendering module 108 takes the $\sigma'_t$ value whose solution $I_D(d)$ to Eq. (6) most closely matches the measured $I(d)$ according to $\|I_D(d)-I(d)\|^2$. To efficiently determine the $\sigma'_t$ in the current implementation, a coarse-to-fine search is employed.

Figure 4:
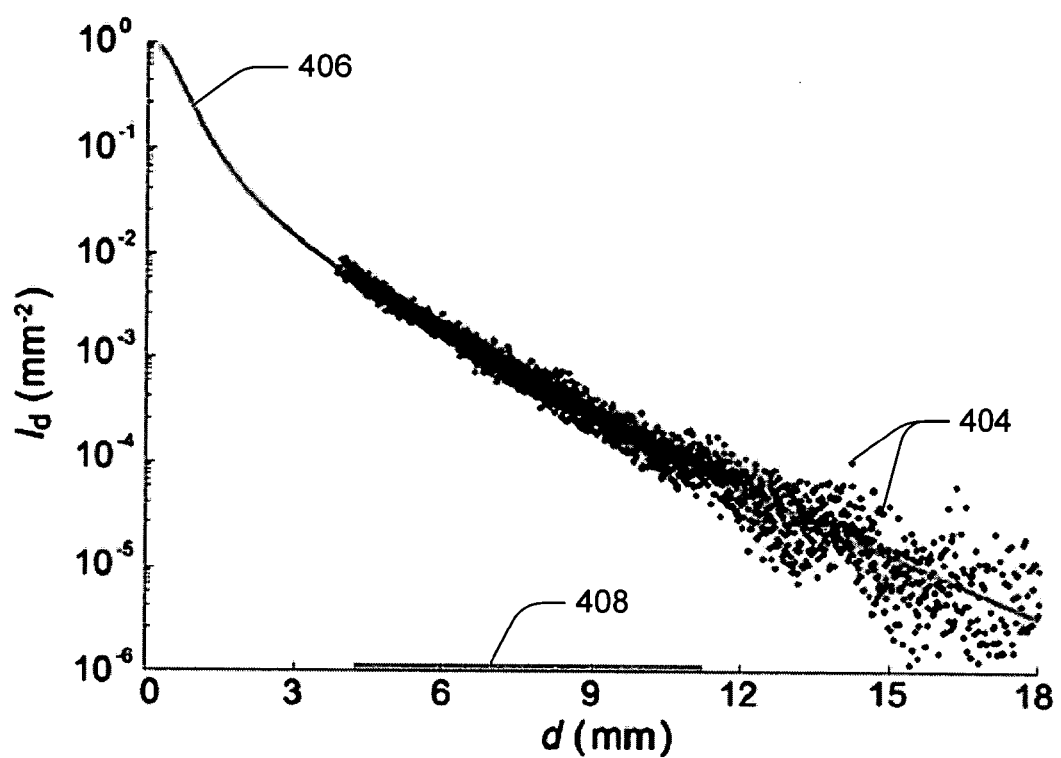
FIG. 4 shows exemplary comparison of dipole diffusion intensities measured from sponge data, and values computed from recovered scattering values.

FIG. 4 shows an exemplary comparison of dipole diffusion intensities measured from sponge data, and values computed from recovered scattering values. More particularly, data values represented by respective dots (e.g., data values 404) respectively represent sponge data values, and data value curve 406 represents data values computed from recovered scattered data values 404. Line segment 408, shown at the bottom of the graph, represents an exemplary user-specified range used to estimate the dipole diffusion parameters. The effectiveness of the described exemplary dipole diffusion parameters is illustrated in FIG. 4, wherein $I(d)$ values (i.e., data values 404) measured from a real sponge, and the curve 406 represents $I_D(d)$ values computed with the dipole approximation from the recovered values of $\alpha'$ and $\sigma'_t$.

Exemplary Mesostructure Exiting Function

From the image set captured for estimating the dipole parameters (i.e., a respective portion of image data 112), modeling and rendering module 108 solves the mesostructure exiting function using the dipole model in Eq. (5) as follows:

$$f_v(p, \omega_o) = \sum_l I(p, v, l) \sum_l I(p, l),$$

Essentially, this represents the image residual after factoring out global dipole diffusion. Since multiple scattering in global light transport is directionally independent, Eq. (3) can be determined independently of incident light direction.

Exemplary Local Reflectance Function

At this point, capture device 120 captures halogen lamp images (i.e., respective portions of image data 112) of the material sample with different lighting directions and viewpoints, as outlined in the "Third Pass" of Table 1. The acquired images include both local and global lighting effects. To obtain an LRF that represents only local scattering, modeling and rendering module 108 computes the global component from the determined dipole parameters and mesostructure entrance/exiting functions, then subtracts this global component from the captured data as follows:

$$R(x_o, \omega_i, \omega_o) = I(x_o, \omega_i, \omega_o) - \sum_{x_i \neq x_o} f_v(x_o, \omega_o) R_d(x_i, x_o) L(x_i, \omega_i) f(\omega_i).$$

Although the dipole diffusion model is not intended to model light transport through inhomogeneous local volumes, some portion of the local scattering is allowed to be represented by the light transport, instead of being fully modeled in the LRF. This substantially avoids having to specify the extent of area $B_o$ in Eq. (4). Subtracting the dipole component in the local area may lead to negative values, but these are not errors and are used to obtain the correct rendering result. For any negative values in the final rendering result due to noise or measurement errors, modeling and rendering module 108 simply truncates such values to zero before tone mapping. Since the sampled laser and lamp positions are not identical due to the structure of the exemplary capture device 120, mesostructure entrance function values at the lamp directions are bilinearly interpolated from the four nearest laser directions.

Exemplary Rendering

During rendering operations, modeling and rendering module 108 textures two components of material model 114 over a mesh surface 116: the mesostructure exiting function and the local reflectance function. One of the other components, the mesostructure entrance function, is uniform over a surface 116, so it is does not need to be textured. The final component, the dipole diffusion parameters, is also not textured over the surface 116. The contribution of dipole diffusion to object 118 appearance is computed at run time with respect to the dipole diffusion parameters and the shape of the object 118 (i.e., the corresponding mesh 116) to be rendered. Given the dipole parameters and object shape, there exist efficient dipole algorithms that can compute the global light transport (dipole) contribution to appearance.

As a material model 114, the quasi-homogeneous material acquired from real samples can be applied to arbitrary objects. For this purpose, modeling and rendering module 108 reorganizes captured image data 112 as a 2-D texture T(x,y) defined on the reference plane. For purposes of exemplary illustration, such 2-D texture is shown as a respective portion of "other data" 122. Each texel $T(x_i, y_i)$ in the texture data includes the reflectance function values and mesostructure exiting function at $(x_i, y_i)$. Modeling and rendering module 108 synthesizes the texture T(x,y) onto the target surface mesh 116, while maintaining consistency in surface appearance under different lighting and viewing directions. Modeling and rendering module 108 directly assigns scattering properties to the resulting formed quasi-homogeneous object 118 for simulating global light transport within its volume.

Quasi-homogeneous objects 118 formed from this material model 114 are straightforward to render. To evaluate the radiance of a surface point $\chi_o$ under a given lighting condition, modeling and rendering module 108 attenuates the incoming radiance on object surface according to the mesostructure entrance function. The diffuse light transport beneath the surface is then evaluated using the dipole approximation and modified by the mesostructure exiting function texture mapped onto the surface. For the local scattering effects, modeling and rendering module 108 directly integrates the local reflectance function on $\chi_o$ over the incoming radiance at $\chi_o$. As a result, both appearance variations over the surface of the quasi-homogenous material object 118, and the scattering effects inside the object volume, are evaluated with material model 114.

To render the LRF, existing hardware-accelerated BTF rendering methods can be utilized, while an efficient dipole algorithm can be used to compute global light transport. With these methodologies, the local and global contributions are rapidly computed and added together to give the rendering result.

Figure 5:
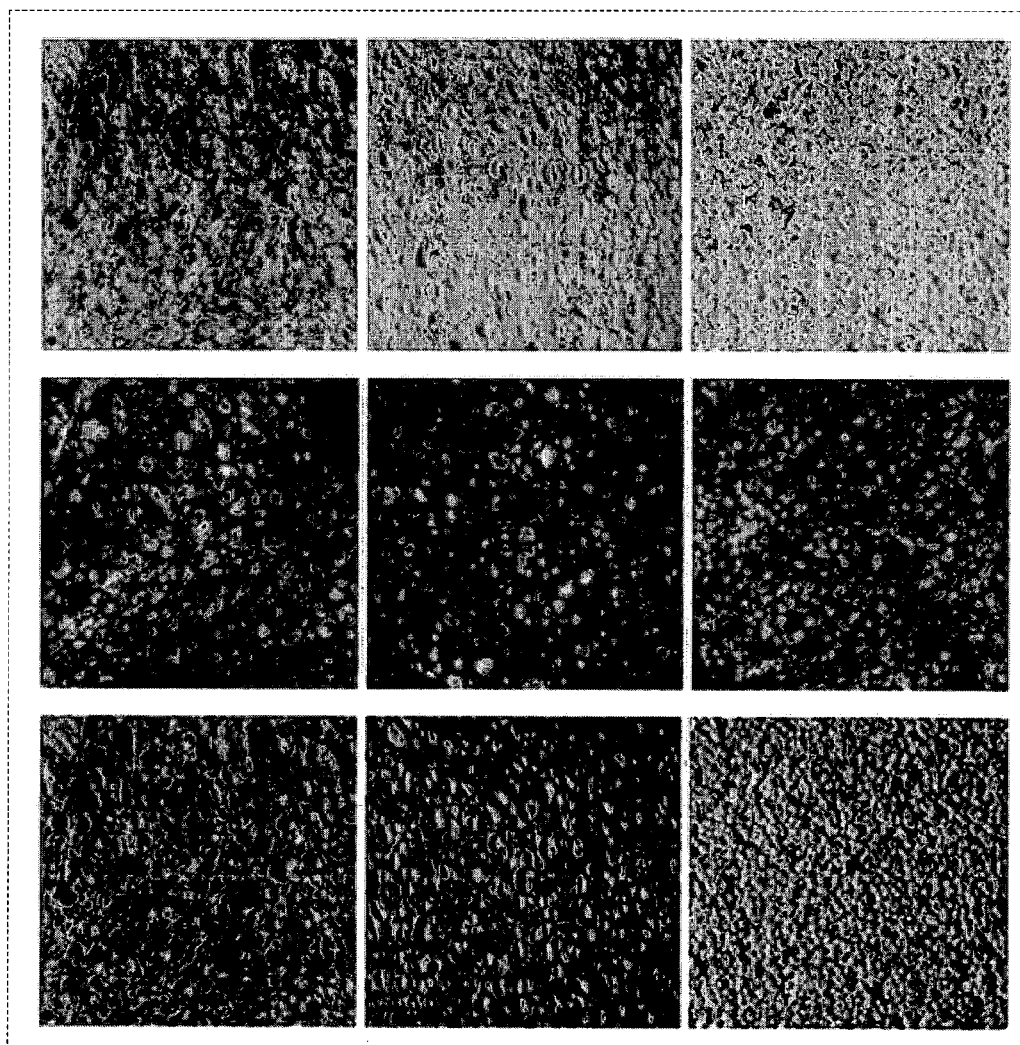
FIG. 5 shows exemplary physical samples acquired by an image capture device, respective ones of which are subsequently modified by a quasi-homogenous material representation module.

FIG. 5 shows exemplary physical samples acquired by image capture device 120 of FIG. 1, and generated by quasi-homogenous material representation module 108 (modeling and rendering module 108). More particularly, images in the top row are exemplary lamp images; images in the middle row are the result of exemplary mesostructure exiting functions; and, images in the bottom row illustrate exemplary results of local reflectance functions.

Exemplary Procedure

Figure 6:
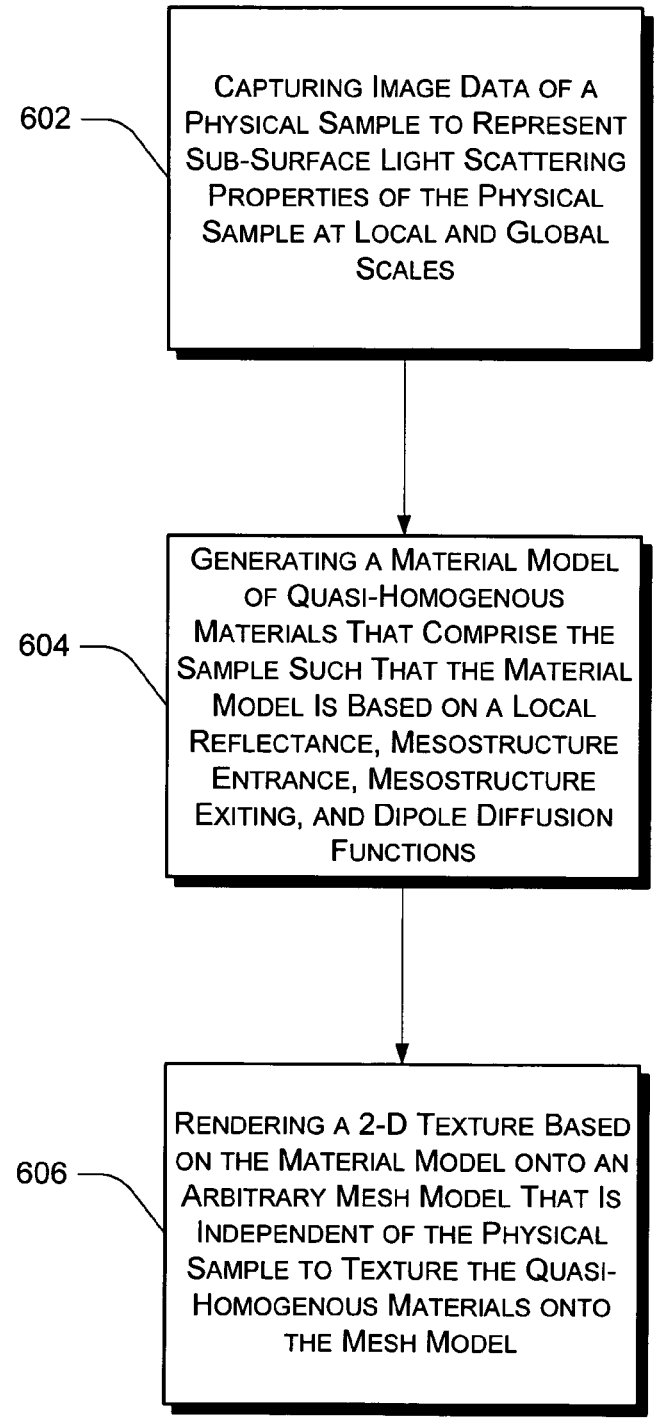
FIG. 6 shows an exemplary procedure for representing quasi-homogenous materials, according to one embodiment.

FIG. 6 shows an exemplary procedure for representing quasi-homogenous materials. For purposes of discussion and exemplary illustration, operations of this procedure are described with respect to components of FIG. 1. The leftmost digit of a component reference number identifies the particular figure in which the component first appears. At block 602, system 100 (FIG. 1) captures image data 112 of a physical sample to represent the sub-surface light scattering properties of the physical sample at local and global scales. At block 604, modeling and rendering module 108, generates a material model 114 of quasi-homogenous materials that make-up the sample. The material model is based on a local reflectance function, a mesostructure entrance function, a mesostructure exiting function, and a dipole diffusion function/parameters. At block 606, modeling and rendering model 108 renders a 2-D texture based on the material model 114 onto an arbitrary mesh model 116. The arbitrary mesh model is independent of the physical sample used to generate the material model 114 representing the quasi-homogenous materials of the physical sample. The rendering operations render the quasi-homogenous materials onto the surface of the mesh model based on the material model.

An Exemplary Operating Environment

Figure 7:
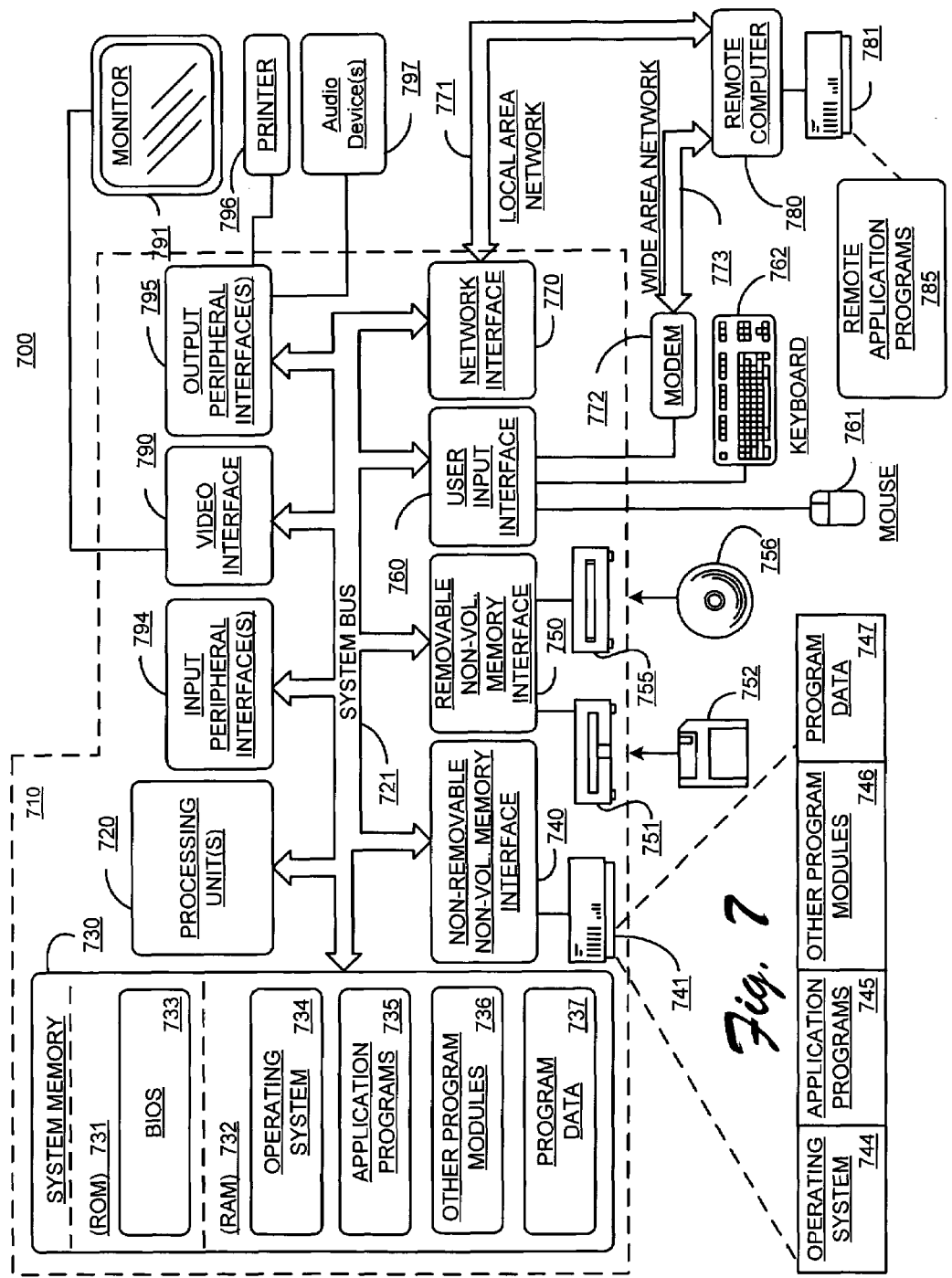
FIG. 7 illustrates an example of a suitable computing environment in which representing quasi-homogenous materials may be fully or partially implemented.

FIG. 7 illustrates an example of a suitable computing environment in which representing quasi-homogenous materials may be fully or partially implemented. Exemplary computing environment 700 is only one example of a suitable computing environment for the exemplary system 100 of FIG. 1 and exemplary operations of FIG. 7, and is not intended to suggest any limitation as to the scope of use or functionality of systems and methods the described herein. Neither should computing environment 700 be interpreted as having any dependency or requirement relating to any one or combination of components illustrated in computing environment 700.

The methods and systems described herein are operational with numerous other general purpose or special purpose computing system, environments or configurations. Examples of well-known computing systems, environments, and/or configurations that may be suitable for use include, but are not limited to personal computers, server computers, multiprocessor systems, microprocessor-based systems, network PCs, minicomputers, mainframe computers, distributed computing environments that include any of the above systems or devices, and so on. Compact or subset versions of the framework may also be implemented in clients of limited resources, such as handheld computers, or other computing devices. The invention, although not required, may be practiced in a distributed computing environment where tasks are performed by remote processing devices that are linked through a communications network. In a distributed computing environment, program modules may be located in both local and remote memory storage devices.

With reference to FIG. 7, an exemplary system providing representing quasi-homogenous materials includes a general-purpose computing device in the form of a computer 710 implementing, for example, system 100 of FIG. 1. Components of computer 710 may include, but are not limited to, processing unit(s) 720, a system memory 730, and a system bus 721 that couples various system components including the system memory to the processing unit 720. The system bus 721 may be any of several types of bus structures including a memory bus or memory controller, a peripheral bus, and a local bus using any of a variety of bus architectures. By way of example and not limitation, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

A computer 710 typically includes a variety of computer-readable media. Computer-readable media can be any available media that can be accessed by computer 710, including both volatile and nonvolatile media, removable and non-removable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 710.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example and not limitation, communication media includes wired media such as a wired network or a direct-wired connection, and wireless media such as acoustic, RF, infrared and other wireless media. Combinations of the any of the above should also be included within the scope of computer-readable media.

System memory 730 includes computer storage media in the form of volatile and/or nonvolatile memory such as read only memory (ROM) 731 and random access memory (RAM) 732. A basic input/output system 733 (BIOS), containing the basic routines that help to transfer information between elements within computer 710, such as during start-up, is typically stored in ROM 731. RAM 732 typically contains data and/or program modules that are immediately accessible to and/or presently being operated on by processing unit 720. By way of example and not limitation, FIG. 7 illustrates operating system 734, application programs 735, other program modules 736, and program data 737.

The computer 710 may also include other removable/non-removable, volatile/nonvolatile computer storage media. By way of example only, FIG. 7 illustrates a hard disk drive 741 that reads from or writes to non-removable, nonvolatile magnetic media, a magnetic disk drive 751 that reads from or writes to a removable, nonvolatile magnetic disk 752, and an optical disk drive 755 that reads from or writes to a removable, nonvolatile optical disk 756 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 741 is typically connected to the system bus 721 through a non-removable memory interface such as interface 740, and magnetic disk drive 751 and optical disk drive 755 are typically connected to the system bus 721 by a removable memory interface, such as interface 750.

The drives and their associated computer storage media discussed above and illustrated in FIG. 7, provide storage of computer-readable instructions, data structures, program modules and other data for the computer 710. In FIG. 7, for example, hard disk drive 741 is illustrated as storing operating system 744, application programs 745, other program modules 746, and program data 747. Note that these components can either be the same as or different from operating system 734, application programs 735, other program modules 736, and program data 737. Operating system 744, application programs 745, other program modules 746, and program data 747 are given different numbers here to illustrate that they are at least different copies.

A user may enter commands and information into the computer 710 through input devices such as a keyboard 762 and pointing device 761, commonly referred to as a mouse, trackball or touch pad. Other input devices (not shown) may include a microphone, joystick, graphics pen and pad, satellite dish, scanner, or the like. These and other input devices are often connected to the processing unit 720 through a user input interface 760 that is coupled to the system bus 721, but may be connected by other interface and bus structures, such as a parallel port, game port or a universal serial bus (USB).

A monitor 791 or other type of display device is also connected to the system bus 721 via an interface, such as a video interface 790. In addition to the monitor, computers may also include other peripheral output devices such as printer 796 and audio device(s) 797, which may be connected through an output peripheral interface 795.

The computer 710 operates in a networked environment using logical connections to one or more remote computers, such as a remote computer 780. In one implementation, remote computer 780 represents computing device 102 of FIG. 1. The remote computer 780 may be a personal computer, a server, a router, a network PC, a peer device or other common network node, and as a function of its particular implementation, may include many or all of the elements described above relative to the computer 710, although only a memory storage device 781 has been illustrated in FIG. 7. The logical connections depicted in FIG. 7 include a local area network (LAN) 781 and a wide area network (WAN) 773, but may also include other networks. Such networking environments are commonplace in offices, enterprise-wide computer networks, intranets and the Internet.

When used in a LAN networking environment, the computer 710 is connected to the LAN 771 through a network interface or adapter 770. When used in a WAN networking environment, the computer 710 typically includes a modem 772 or other means for establishing communications over the WAN 773, such as the Internet. The modem 772, which may be internal or external, may be connected to the system bus 721 via the user input interface 760, or other appropriate mechanism. In a networked environment, program modules depicted relative to the computer 710, or portions thereof, may be stored in the remote memory storage device. By way of example and not limitation, FIG. 7 illustrates remote application programs 785 as residing on memory device 781. The network connections shown are exemplary and other means of establishing a communications link between the computers may be used.

Conclusion

Although the systems and methods for representing quasi-homogenous materials have been described in language specific to structural features and/or methodological operations or actions, it is understood that the implementations defined in the appended claims are not necessarily limited to the specific features or actions described. Rather, the specific features and operations of system 100 are disclosed as exemplary forms of implementing the claimed subject matter.

The invention claimed is:

1. A computer-implemented method comprising:
  modeling quasi-homogenous materials to generate a material model of a physical sample, the material model indicating how light is scattered by the quasi-homogenous materials, the modeling comprising:
    separating appearance components from input image data that corresponds to elements of the material model to enable inverse rendering of dipole diffusion parameters and measurement of texture functions; and wherein the material model provides information useful for texturing surfaces of arbitrary types and sizes of mesh models with the quasi-homogenous materials.

2. The method of claim 1, wherein modeling the quasi-homogenous materials is based on a bidirectional scattering-surface reflectance-distribution function to obtain sub-surface scattering properties at local and global scales.

3. The method of claim 1, wherein the material model does not capture actual appearance of the physical sample.

4. The method of claim 1, wherein the material model comprises indications of how light is scattered to effect local surface points of the physical sample independent of light propagation within a whole of the physical sample.

5. The method of claim 1, wherein the material model indicates sub-surface light scattering characteristics of the quasi-homogenous materials analyzed at local and global scales.

6. The method of claim 1, wherein the material model to respectively measures sub-surface light scattering based on scales of local material heterogeneity and global material homogeneity.

7. The method of claim 1, wherein the modeling further comprises:
generating, by a capture device, or receiving, from the capture device, image input data; and
modeling the quasi-homogenous materials from the image input data to generate the material model.

8. The method of claim 7, wherein the image data represents global and local light scattering separately captured using different types of lighting.

9. The method of claim 7, wherein the image data represents global and local light scattering captured with a combination of a laser stripe and lamps, and not a laser beam.

10. The method of claim 7, wherein the capture device comprises a turntable, and imaging array, a lighting array, and a laser scan unit.

11. The method of claim 7, wherein the capture device comprises an imaging array, a lighting array, and a laser scan unit, the imaging array, the imaging array and the lighting array and the laser scan unit being respectively mounted on two concentric arcs centered around a turntable for placing the physical sample.

12. A computer-implemented method comprising:
modeling quasi-homogenous materials to generate a material model of a physical sample, the material model indicating how light is scattered by the quasi-homogenous materials; the material model providing information useful for texturing surfaces of arbitrary types and sizes of mesh models with the quasi-homogenous materials; and
wherein the material model comprises a homogenous sub-surface scattering component for global light transport, a local reflectance function, a mesostructure entrance function, and a mesostructure exiting function.

13. The method of claim 12, wherein the local reflectance function, the mesostructure entrance function, and the mesostructure exiting function account for local scattering effects that respectively include non-homogenous local sub-surface scattering, surface reflections from mesostructure, and locally non-homogenous mesostructure affects entering and exiting material of the physical sample.

14. A computer-implemented method comprising:
modeling quasi-homogenous materials to generate a material model of a physical sample, the material model indicating how light is scattered by the quasi-homogenous materials; the material model providing information useful for texturing surfaces of arbitrary types and sizes of mesh models with the quasi-homogenous materials:
reorganizing information and the material model to generate a 2-D texture defined on a reference plane;
rendering the 2-D texture onto a target surface mesh, the rendering directly assigning scattering properties to the object for simulating global light transport within the volume of the object to maintain consistency in surface appearance under different lighting and viewing directions; and
wherein the target surface mesh represents an arbitrary object.

15. The method of claim 14, wherein the rendering further comprises evaluating radiance of a surface point under a given lighting condition by:
attenuating incoming radiance on surface of the object according to a mesostructure entrance function;
evaluating diffuse light transport beneath the surface using a dipole approximation modified by a mesostructure exiting function texture mapped onto the surface; and
integrating a local reflectance function on the surface point over incoming radiance at the surface point.

16. A computer-implemented method comprising:
modeling quasi-homogenous materials to generate a material model of a physical sample, the material model indicating how light is scattered by the quasi-homogenous materials, the modeling further comprising:
creating image input data to generate the material model of model the quasi-homogenous materials; and
wherein creating further comprises:
scanning the physical sample with laser stripes emitted from different light directions;
scanning the physical sample from different viewing directions and under vertically projected illumination; and
capturing images from the physical sample with different lighting directions and viewpoints; and
wherein the material model provides information useful for texturing surfaces of arbitrary types and sizes of mesh models with the quasi-homogenous materials.

* * * * *